United States Patent
Carriazo

(10) Patent No.: US 9,655,597 B2
(45) Date of Patent: May 23, 2017

(54) MEDICAL HOLLOW NEEDLE

(71) Applicant: Cesar C. Carriazo, Barranquilla (CO)

(72) Inventor: Cesar C. Carriazo, Barranquilla (CO)

(*) Notice: Subject to any disclaimer, the term of this patent is extended or adjusted under 35 U.S.C. 154(b) by 41 days.

(21) Appl. No.: 14/230,306

(22) Filed: Mar. 31, 2014

(65) Prior Publication Data

US 2015/0272780 A1    Oct. 1, 2015

(51) Int. Cl.
    *A61B 10/02*    (2006.01)
    *A61F 9/007*    (2006.01)
    *A61B 17/34*    (2006.01)
    *A61B 17/32*    (2006.01)
    *A61F 9/008*    (2006.01)

(52) U.S. Cl.
CPC .. *A61B 10/0266* (2013.01); *A61B 17/320016* (2013.01); *A61B 17/3421* (2013.01); *A61F 9/00745* (2013.01); *A61F 2009/0087* (2013.01); *A61F 2009/00887* (2013.01)

(58) Field of Classification Search
CPC ........ A61B 17/320016; A61B 10/0266; A61B 17/3417; A61B 2017/320072; A61F 9/00745; A61M 5/3286
See application file for complete search history.

(56) References Cited

U.S. PATENT DOCUMENTS

| | | | |
|---|---|---|---|
| 3,965,901 A * | 6/1976 | Penny | A61M 25/007 604/119 |
| 4,643,717 A | 2/1987 | Cook et al. | |
| 4,689,040 A * | 8/1987 | Thompson | A61B 17/22004 604/22 |
| 4,959,049 A | 9/1990 | Smirmaul | |
| 5,843,048 A * | 12/1998 | Gross | A61B 17/3401 604/264 |
| 8,162,966 B2 * | 4/2012 | Connor | A61B 17/320016 606/160 |
| 2012/0197215 A1 | 8/2012 | Akahoshi | |

* cited by examiner

*Primary Examiner* — Bradley Osinski
(74) *Attorney, Agent, or Firm* — Miles and Stockbridge P.C.

(57) ABSTRACT

A medical hollow needle for use with at least a suction device includes at least one suction tube or suction line with a lumen and having a proximal end and a distal end, wherein the distal end is formed as a suction aperture, and a needle tip formed at said distal end of the suction tube or suction line, wherein said needle tip is formed spoon-like and protrudes beyond an edge of said suction aperture or said distal end of said suction tube or suction line.

10 Claims, 4 Drawing Sheets

MEDICAL HOLLOW NEEDLE

FIELD

The present invention relates to a medical hollow needle for use with at least a suction device.

BACKGROUND INFORMATION

Today, the opacity of the eye lens referred to as cataract is a very frequent disease, by which in particular elder humans are afflicted. The only possibility of correction is the surgical treatment. It consists in removing the anterior lens capsule, cortex of lens and lens core with subsequent implantation of a so-called intraocular lens (IOL), which is introduced into the lens capsular bag and may consist of different materials.

Therein, the eye lens is removed by so-called phacoemulsification. Therein, the eye lens is destroyed employing ultrasound and is sucked off. For this purpose, a thin medical hollow needle is introduced into the eye lens, wherein the hollow needle is vibrated by an ultrasonic generator. Thereby, the eye lens is decomposed into small fragments, which can then be sucked off through the medical hollow needle. For supporting the disintegration of the eye lens, a second medical instrument is usually introduced into the eye lens via a second step. Therein, the introduction end of this second medical instrument can be formed spoon-like or hoe-like and supports the fragmentation of the eye lens by means of the oscillating hollow needle. In particular with very hard lens cores, this second medical instrument has to be introduced for supporting the complete fragmentation of the eye lens. However, this is disadvantageous in that increased stress of the patient occurs by the introduction of two instruments into the eye lens.

Therefore, embodiments of the invention provide a medical hollow needle of the initially mentioned kind, which ensures increased efficiency and lower stress of a patient in phacoemulsification.

SUMMARY

Embodiments of the present invention relate to a medical hollow needle for use with at least a suction device, said needle comprising at least one suction tube or suction line with a lumen and having a proximal end and a distal end, wherein the distal end is formed as a suction aperture, and a needle tip formed at said distal end of the suction tube or suction line. Said needle tip is formed spoon-like and protrudes beyond an edge of said suction aperture or said distal end of said suction tube or suction line. Said spoon-like tip comprising a proximal end connected to said distal end of said suction tube or suction line, a distal end facing away from said distal end of said suction tube or suction line and a middle portion located between said proximal and distal ends, wherein the middle portion having an extension which at least partly extends beyond an outer diameter of said suction tube or suction line. By the formation of said spoon-like projection protruding beyond the edge of the suction aperture and the distal end of the suction tube or suction line, portions of the eye, which are located on the side facing away from the suction aperture of the spoon-like projection, are protected. Thereby an enhanced suction power during the surgical intervention can be applied, without running the risk of inadvertently damaging parts of the eye due to the raised suction performance. Owing to the increased suction capacity also the duration of the surgical operation can be considerably reduced, which is equally advantageous to the patient.

According to other embodiments of the medical hollow needle said distal end of said spoon-like tip is at least partly rounded or comprises an end wall disposed generally perpendicular to longitudinal extension of said tip.

Other embodiments of the medical hollow needle include a projection which is circularly, fan-shaped/fan-like, shovel-shaped/shovel-like, thorn-shaped/thorn-like, needle-shaped/needle-like, or hoe-shaped/hoe-like formed. Other shapes are also conceivable. In addition, there is the possibility that the projection is formed narrowing in the distal direction or tapering in the distal direction. Further possibilities of configuration of the projection provide at least one blade on the projection.

The respective shape of the projection also depends on the state of the eye lens to be fragmented among other things. According to the present degree of hardness of the eye lens, a shape of the projection optimized for the surgical procedure can be selected. Thus, for example, the projection can have a blade in case of the presence of a very hard eye lens, by which the fragmentation effect of the oscillating hollow needle is considerably increased.

According to another embodiment of the medical hollow needle, the projection can be integrally formed with the distal end of the suction tube or suction line. However, it is also possible that the projection is formed as a separate element and correspondingly connected to the distal end of the suction tube or suction line. In the first mentioned case, the medical hollow needles according to the invention can in particular be medical hollow needles for single use. In the last mentioned case, the projection can be replaced and exchanged according to requirement.

According to another embodiment of the medical hollow needle the hollow needle has at least one additional sucking aperture formed in the suction tube or suction line in the region of its distal end. Besides the actual suction aperture disposed at the distal end, the additional suction aperture in the wall of the distal end of the hollow needle can considerably increase the suction effect. Thus, advantageously, the fragmented parts of the eye lens can be fast removed through the suction tube or suction line. This also advantageously shortens the duration of the surgical procedure and thus lowers the stress for the patient.

According to other embodiments the medical hollow needle comprises further at least one connection means for connecting said needle to at least one of a one suction device, an ultrasound generating device, an irrigation device, or medical laser device.

BRIEF DESCRIPTION OF THE DRAWINGS

Further features of the invention are apparent from the claims, the embodiments as well as based on the drawings. The features and feature combinations mentioned above in the description as well as the features and feature combinations mentioned below in the embodiments are usable not only in the respectively specified combination, but also in other combinations without departing from the scope of the invention. The components in the following figures are not necessarily drawn to scale. Instead, emphasis is placed upon clearly illustrating the general principles of the present disclosure. Reference characters designating corresponding components are repeated as necessary throughout the figures for the sake of consistency and clarity.

DETAILED DESCRIPTION

Figure 1:
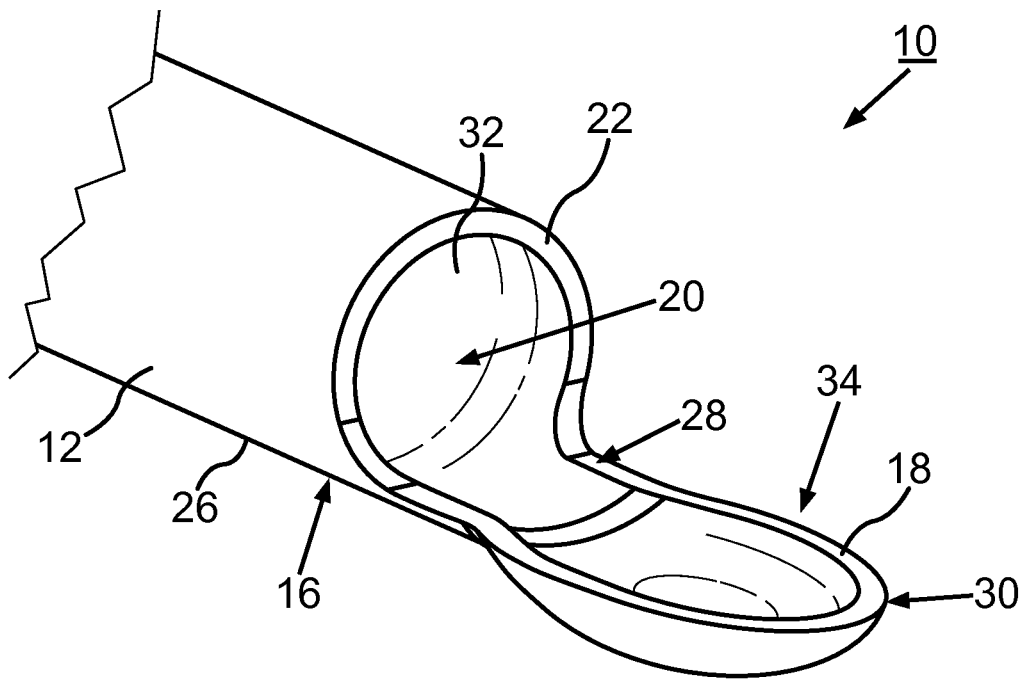
FIG. 1 shows a schematic illustration of a distal end of a medical hollow needle according to one embodiment of the invention.

FIG. 1 shows a schematic illustration of a distal end 16 of a medical hollow needle 10 according to an embodiment of the invention. Therein, the hollow needle 10 is provided for use with a suction device (not shown). The hollow needle 10 includes a suction tube or suction line 12 with a proximal end (not shown) distal from the body of a patient and the distal end 16 proximal to the body, wherein the distal end 16 is formed as a suction aperture 20. The suction aperture 20 is approximately circularly formed in cross-section according to this embodiment of the hollow needle 10 and forms the distal end of a lumen 32 of said suction tube or suction line 12. Said proximal end of said suction tube or suction line 12 comprises at least one connection means for connecting said needle 10 to at least one of a suction device, an ultrasound generating device, an irrigation device, or medical laser device (not shown).

Further, a needle tip 18 is disposed on the suction aperture 20 at the distal end 16 of the suction tube or suction line 12. Said needle tip 18 protrudes beyond an edge 22 of the suction aperture 20 and the distal end 16 of the suction tube or suction line 12. Said edge 22 of the suction aperture 20 is not continuously formed. A part of the edge 22 is preset or formed by the needle tip 18. Further, said suction tube or suction line 12 comprises a bottom wall 26 and said tip 18 is an extension of said bottom wall 26. The needle tip 18 is formed spoon-like. Said spoon-like tip 18 comprising a proximal end 28 connected to said distal end 16 of said suction tube or suction line 12, a distal end 30 facing away from said distal end 16 of said suction tube or suction line 12 and a middle portion 32 located between said proximal and distal ends, wherein the middle portion 32 has an extension which at least partly extends beyond an outer diameter of said suction tube or suction line 12. Moreover, the concave portion of the spoon-like tips 18 is formed in such a way that it protrudes beyond the outer circumference of the bottom wall 26 of the suction tube or suction line 12. Said distal end 30 of said spoon-like tip 18 is curved or rounded, respectively.

The needle tip 18 is formed integrally with the bottom wall 26 of the suction tube or suction line 12. But it is possible that said spoon-like tip 18 is formed as a separate element and is connected to said distal end 16 of said suction tube or suction line 12.

Figure 2:
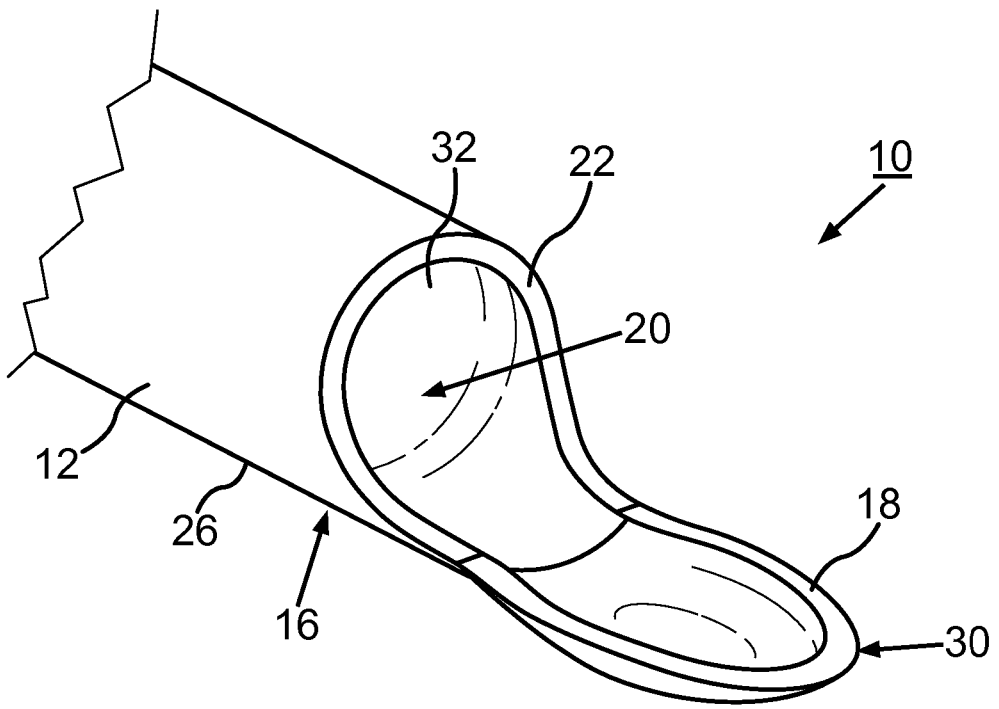
FIG. 2 shows a schematic illustration of a distal end of a medical hollow needle according to another embodiment of the invention.

FIG. 2 shows a schematic illustration of a distal end 16 of a medical hollow needle 10 according to another embodiment of the invention. The structure of the needle 10 corresponds to that of the embodiment shown in FIG. 1. However, the spoon-like tip 18 is of a narrower design, i.e. it has a somewhat larger longitudinal extension than that of the needle tip shown in FIG. 1. Moreover, the suction aperture 20 at the distal end 16 is formed at a slight angle relative to a longitudinal axis of the suction tube or suction line 12.

Figure 3:
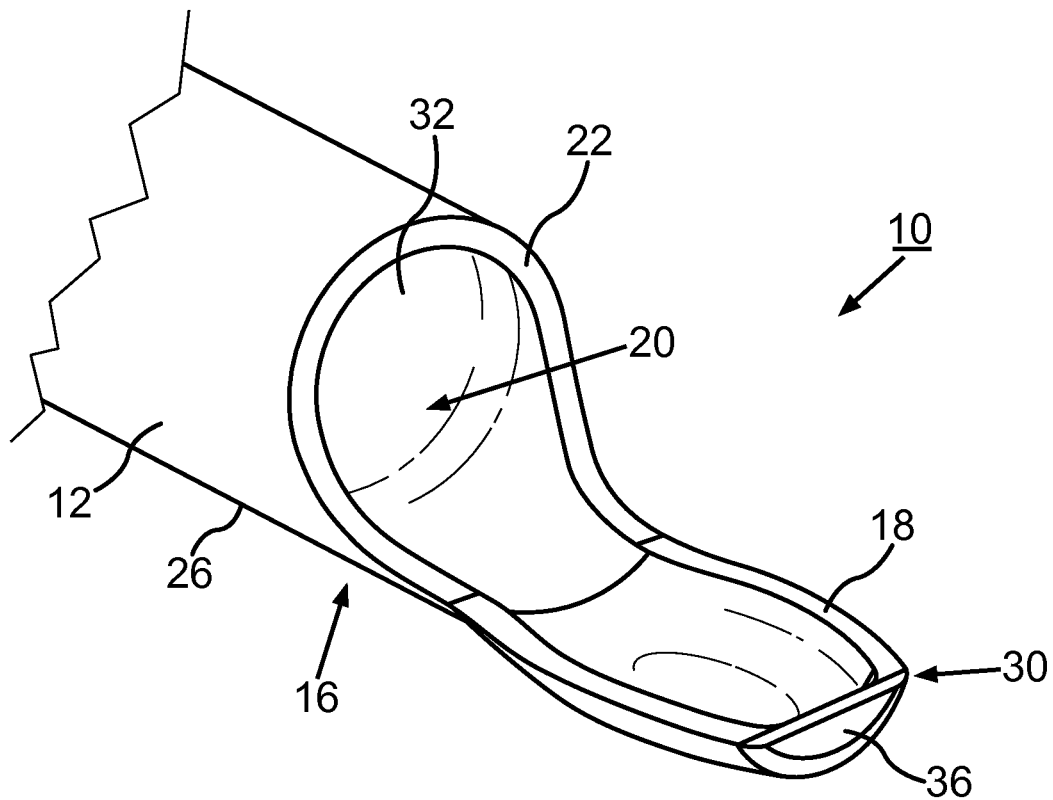
FIG. 3 shows a schematic illustration of a distal end of a medical hollow needle according to another embodiment of the invention.

FIG. 3 shows a schematic illustration of a distal end 16 of a medical hollow needle 10 according to another embodiment of the invention. The structure of the needle 10 in this set-up corresponds to that of the embodiment shown in FIG. 2. However, said distal end 30 of said spoon-like tip 18 comprises an end wall 36 disposed generally perpendicular to a longitudinal extension of said tip 18.

Figure 4:
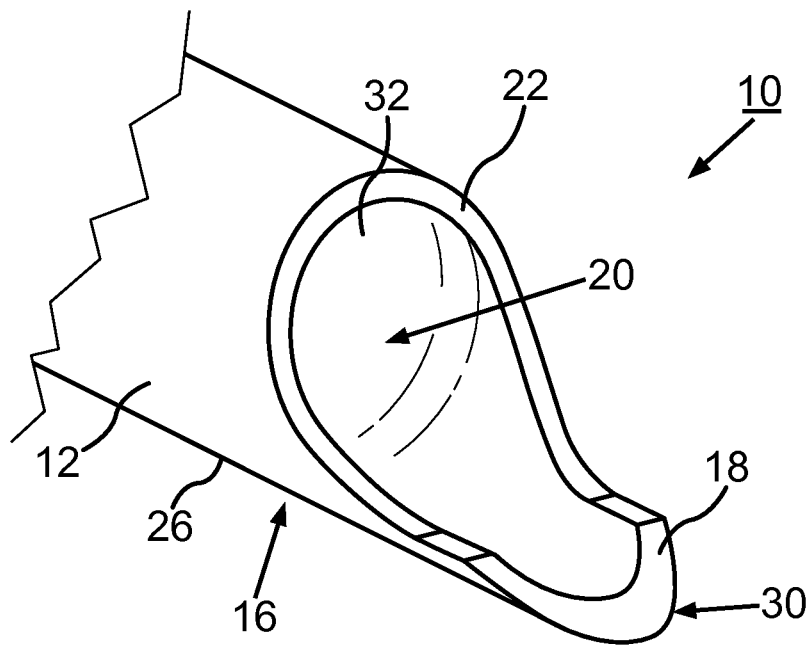
FIG. 4 shows a schematic illustration of a distal end of a medical hollow needle according to another embodiment of the invention.

FIG. 4 shows a schematic illustration of a distal end 16 of a medical hollow needle 10 according to another embodiment of the invention. The hollow needle 10 includes a suction tube or suction line 12 with a proximal end (not shown) distal from the body of a patient and the distal end 16 proximal to the body, wherein the distal end 16 is formed as a suction aperture 20. The suction aperture 20 is approximately oval in cross-section and forms the distal end of a lumen 32 of said suction tube or suction line 12. Said proximal end of said suction tube or suction line 12 comprises at least one connection means for connecting said needle 10 to at least one of a suction device, an ultrasound generating device, an irrigation device, or medical laser device (not shown). Further, a shovel-shaped needle tip 18 is disposed on the suction aperture 20 at the distal end 16 of the suction tube or suction line 12. Said needle tip 18 protrudes beyond an edge 22 of the suction aperture 20 and the distal end 16 of the suction tube or suction line 12. A part of said edge 22 is preset or formed by the needle tip 18. Further, said suction tube or suction line 12 comprises a bottom wall 26 and said tip 18 is an extension of said bottom wall 26. The distal end 30 of said tip 18 is of a slanted/chamfered design.

Figure 5:
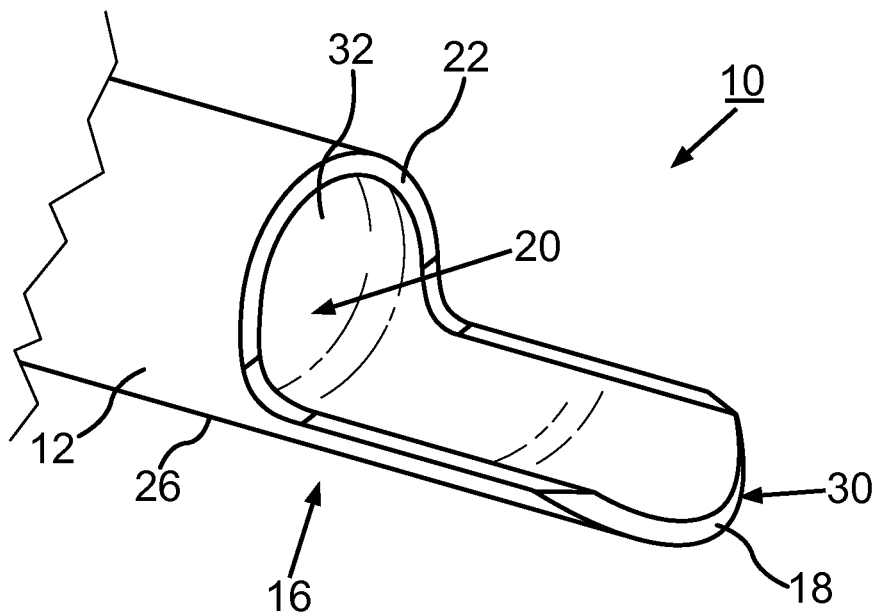
FIG. 5 shows a schematic illustration of a distal end of a medical hollow needle according to another embodiment of the invention.

FIG. 5 shows a schematic illustration of the distal end 16 of a medical hollow needle 10 according to another embodiment of the invention. In contrast to the embodiment shown in FIG. 4, herein, the needle tip 18 again has a concave, shovel-shaped configuration. However, in contrast to the embodiment illustrated in FIG. 4, the transition between the edge 22 of the suction aperture 20 is not slanted/chamfered, but formed at an angle of approximately 90°. One clearly recognizes that the tip 18 is formed protruding beyond the edge 22 of the suction aperture 20 and the distal end 16. Further, said tip 18 comprises a rounded distal end 30.

Figure 6:
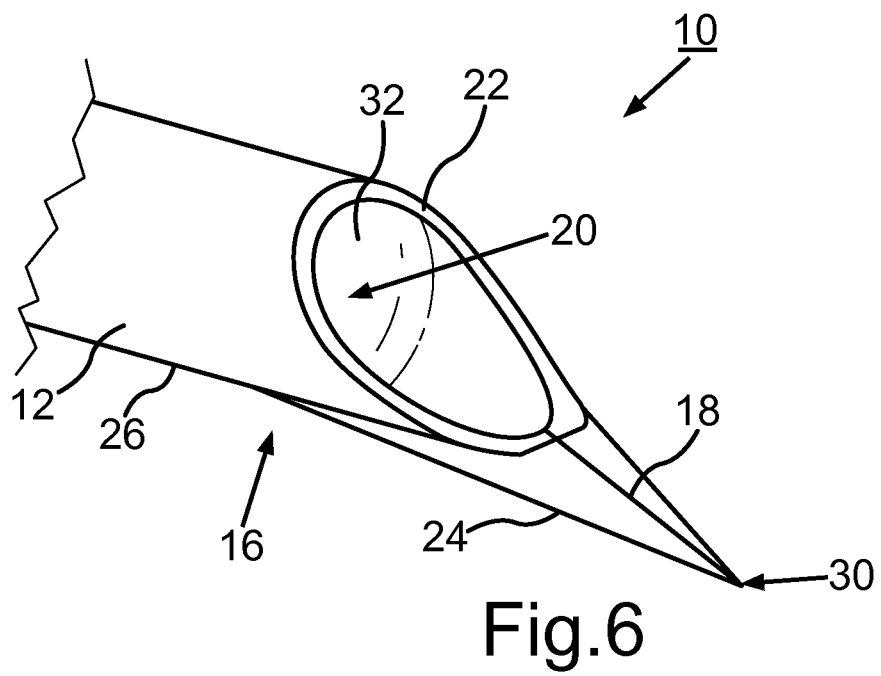
FIG. 6 shows a schematic illustration of a distal end of a medical hollow needle according to another embodiment of the invention.

FIG. 6 shows a schematic illustration of the distal end 16 of a medical hollow needle 10 according to another embodiment of the invention. According to this embodiment, the needle tip 18 is formed tapering in distal direction towards the distal end 30 and comprises a blade 24. The suction aperture 20 has an oval shape in the top view. Overall, the tip 18 protrudes beyond the edge 22 of the suction aperture 20 and the distal end 16 of the suction tube or suction line 12. However, one recognizes that a partial region of the tip 18 with the blade 24 disposed thereon abuts or is formed with said bottom wall 26 of said suction tube or suction line 12 in proximal direction.

Figure 7:
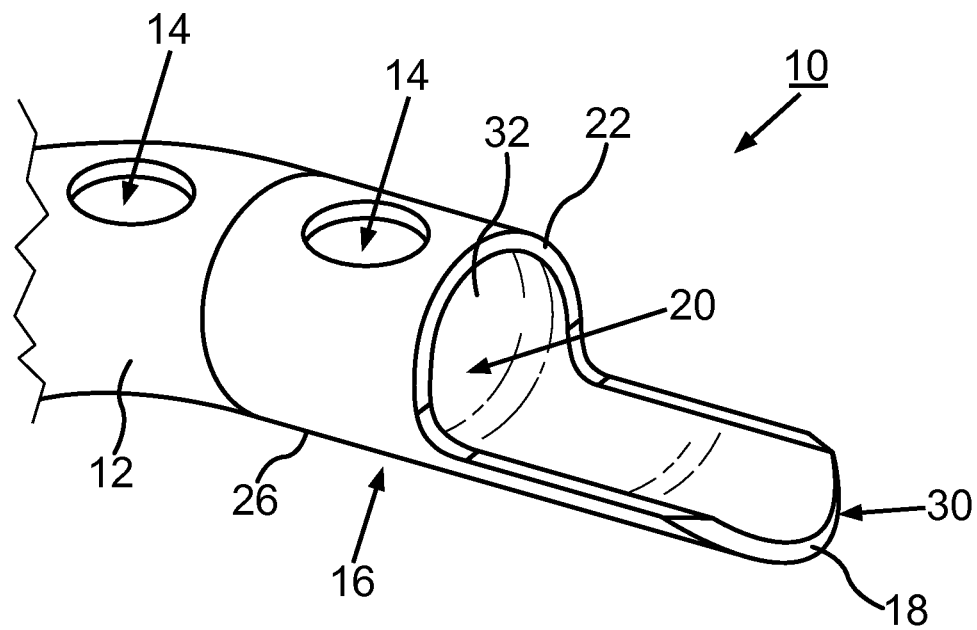
FIG. 7 shows a schematic illustration of a distal end of a medical hollow needle according to another embodiment of the invention.

FIG. 7 shows a schematic illustration of the distal end 16 of the medical hollow needle 10 according to another embodiment of the invention. One recognizes that the needle tip 18 is formed like that in the embodiment described in FIG. 5. In contrast to the afore-mentioned embodiment, the medical hollow needle 10 according to this embodiment has two additional suction apertures 14 formed in the suction tube or suction line 12 in the region of the distal end 16. By these additional suction apertures 14, the suction capacity or the discharge rate through the suction tube or suction line 12 increases considerably.

Figure 8:
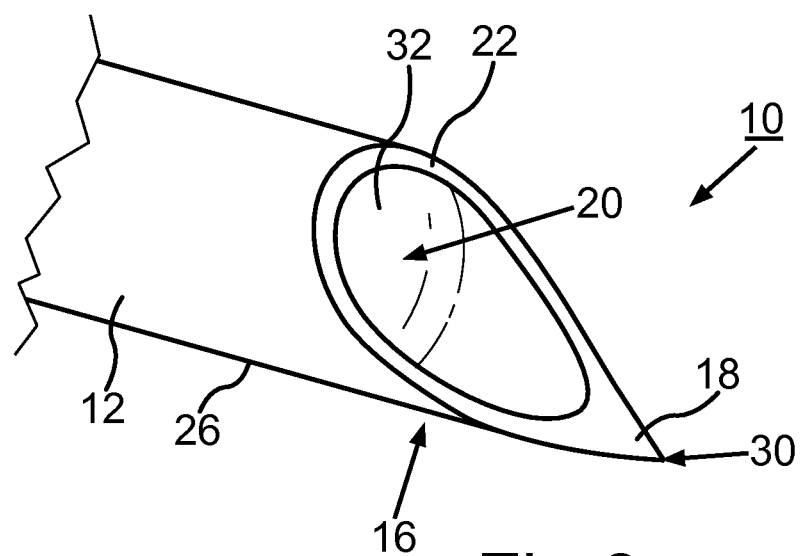
FIG. 8 shows a schematic illustration of a distal end of a medical hollow needle according to another embodiment of the invention.

FIG. 8 shows a schematic illustration of the distal end 16 of the medical hollow needle 10 according to another embodiment of the invention. One recognizes that the needle tip 18 is formed tapering in distal direction towards the distal end 30. The suction aperture 20 has an oval shape in the top view. Overall, the tip 18 protrudes beyond the edge 22 of the suction aperture 20 and the distal end 16 of the suction tube or suction line 12.

The different embodiments of the medical hollow needle 10 described above each have a needle tip 18, which is integrally formed with the suction tube or suction line 12. But it is possible that said tips 18 are formed as separate elements and are connected to the corresponding distal ends 16 of said suction tubes or suction lines 12. Said suction tube or suction line 12 and the needle tip 18 can be made of metal, a metal alloy, of plastic, of ceramic or a combination thereof.

The features, structures, or characteristics of the invention described throughout this specification may be combined in any suitable manner in one or more embodiments. For example, the usage of "one embodiment," "some embodiments," "certain embodiment," "certain embodiments," or other similar language, throughout this specification refers to the fact that a particular feature, structure, or characteristic described in connection with the embodiment may be included in at least one embodiment of the present invention. Thus, appearances of the phrases "one embodiment," "some embodiments," "a certain embodiment," "certain embodiments," or other similar language, throughout this specification do not necessarily all refer to the same group of embodiments, and the described features, structures, or characteristics may be combined in any suitable manner in one or more embodiments.

One having ordinary skill in the art will readily understand that the invention as discussed above may be practiced with elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention.

What is claimed is:

1. A medical hollow needle for use with at least a suction device, said needle comprising:
    at least one suction tube or suction line with a lumen and having a proximal end and a distal end, wherein the distal end is formed as a suction aperture, and
    a needle tip formed as a projection beyond an edge of the suction aperture projecting from said distal end of the suction tube or suction line,
    wherein:
        said needle tip is circularly, fan-shaped, shovel-shaped, thorn-shaped, needle-shaped or hoe-shaped formed;
        said needle tip comprises a proximal end connected to said distal end of said suction tube, a distal end facing away from said distal end of said suction tube or suction line, and a middle portion located between said proximal and distal ends, the middle portion having an extension which at least partly extends beyond an outer diameter of said suction tube or suction line; and
        said suction tube or suction line comprises a central longitudinal axis, wherein the needle tip extends longitudinally from the distal tip without intersecting the central longitudinal axis.

2. The medical hollow needle of claim 1, wherein said needle tip is formed narrowing in the distal direction or tapering in the distal direction.

3. The medical hollow needle of claim 1, wherein said needle tip comprises at least one blade.

4. The medical hollow needle of claim 1, wherein said needle tip is formed integrally with said distal end of said suction tube or suction line.

5. The medical hollow needle of claim 1, wherein said needle tip is formed as a separate element and is connected to said distal end of said suction tube or suction line.

6. The medical hollow needle of claim 5, wherein the separate element is removable from said distal end.

7. The medical hollow needle of claim 1, further comprising at least one additional suction aperture formed in said suction tube or suction line in the region of its distal end.

8. The medical hollow needle of claim 1, further comprising at least one connection means for connecting said needle to at least one of a suction device, an ultrasound generating device, an irrigation device, or medical laser device.

9. The medical hollow needle of claim 1, wherein said suction tube or suction line comprises a bottom wall and said needle tip is an extension of said bottom wall.

10. The medical hollow needle according to claim 1, wherein the needle is configured to be vibrated by an ultrasonic generator during use.

* * * * *